__United States Patent__ [19]

Apple et al.

[11] 4,275,192

[45] Jun. 23, 1981

[54] BIS(4-DEMETHOXYDAUNORUBICIN)-DIHYDRAZONE DERIVATIVES AND PHARMACOLOGICALLY ACCEPTABLE SALTS THEREOF

[75] Inventors: Martin A. Apple, Daly City, Calif.; Raphael Pappo, Skokie, Ill.

[73] Assignee: G. D. Searle & Co., Chicago, Ill.

[21] Appl. No.: 35,657

[22] Filed: May 3, 1979

[51] Int. Cl.³ .................... C07H 15/24; A61K 31/71
[52] U.S. Cl. .................... 536/17 A; 536/4; 536/18; 536/53; 424/180
[58] Field of Search ..................... 536/17 A

[56] References Cited

U.S. PATENT DOCUMENTS

| | | | |
|---|---|---|---|
| 3,957,755 | 5/1976 | Jolles | 536/17 A |
| 4,112,217 | 9/1978 | Henry et al. | 536/17 A |
| 4,125,704 | 11/1978 | Henry et al. | 536/17 A |

OTHER PUBLICATIONS

Tong et al., "Abstract #19," "Second Joint Conference of the Chemical Institute of Canada and the American Chemical Society," Montreal, Canada, May 29–Jun. 2, 1977.

*Primary Examiner*—Johnnie R. Brown
*Attorney, Agent, or Firm*—W. Dennis Drehkoff; Mary Jo Kanady

[57] ABSTRACT

The present invention relates to bis(4-demethoxydaunorubicin)dihydrazone of the formula

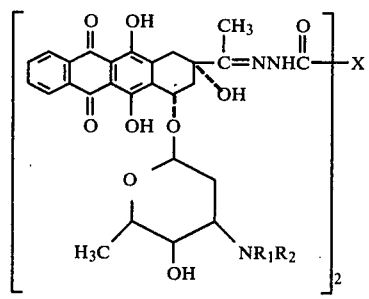

wherein $R_1$ and $R_2$ represent hydrogen or alkyl having from 1 to 4 carbon atoms and X represents
  (a) alkylene having from 3 to 20 carbon atoms and optionally substituted by one or more hydroxy and/or primary amino groups, or
  (b) alkylene optionally interrupted by one or more secondary amino groups, the total number of carbon and nitrogen atoms in the resultant chain being 3 to 20 and to pharmacologically acceptable salts thereof which are potent inhibitors of neoplastic disease and are also useful as antiviral agents.

8 Claims, No Drawings

BIS(4-DEMETHOXYDAUNORUBICIN)DIHYDRAZONE DERIVATIVES AND PHARMACOLOGICALLY ACCEPTABLE SALTS THEREOF

BACKGROUND OF THE INVENTION

1. Field of the Invention

The present invention relates to bis(4-demethoxydaunorubicin)dihydrazones and the pharmacologically acceptable salts thereof which are potent inhibitors of neoplastic disease and also possess antiviral utility.

2. Description of the Prior Art

AACR Abstracts #675 dated March, 1978 describes the use of bis-daunorubicins linked through their C-13 ketones by aminodicarboxylic acid hydrazides as inhibitors of forward transcription (*E. coli* RNA polymerase) or reverse transcription (RSV virus) and as inhibitors of P388 leukemia in mice.

The compounds of the present invention are structurally distinct from the compounds of AARC Abstract #675 in that they do not have the methoxy group at C-4 of the daunomycinone substituent. Compounds lacking the C-4 methoxy are more potent and more effective than those reported in AACR Abstract #675.

SUMMARY OF THE INVENTION

The present invention encompasses compounds of the formula

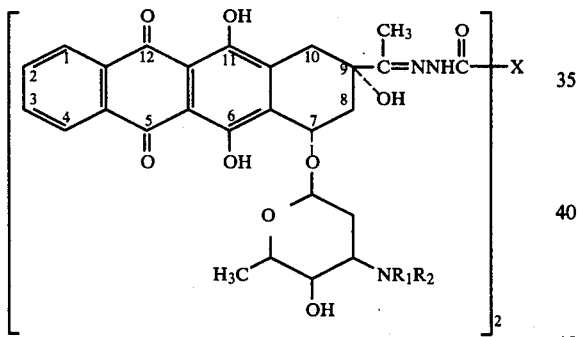

wherein $R_1$ and $R_2$ represent hydrogen or alkyl having from 1 to 4 carbons and X represents (a) alkylene having from 3 to 20 carbon atoms and optionally substituted by one or more hydroxy and/or primary amino groups, or (b) alkylene optionally interrupted by one or more secondary amino groups, the total number of carbon and nitrogen atoms in the resultant chain being from 3 to 20, and salts thereof with acids of the formula

HT wherein T represents 1 equivalent of an anion such as chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like which, in combination with the cationic portion of a salt aforesaid, is neither therapeutically nor otherwise incompatible.

Equivalent to the enformulated compounds for the purposes of this invention are solvates thereof in which pharmacologically insignificant amounts of solvent are present.

A preferred embodiment of the present invention is represented by the formula

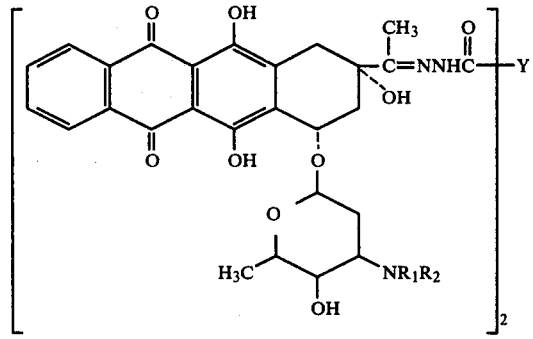

wherein $R_1$ and $R_2$ represent hydrogen or alkyl having 1 to 4 carbon atoms and Y represents

 (a)

 (b)

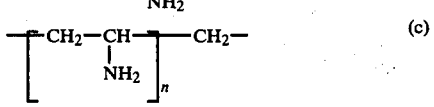 (c)

wherein n is a positive integer from 1 to 9,

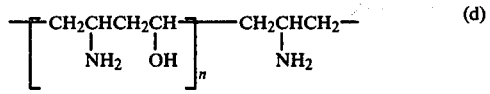 (d)

wherein n is a positive integer from 1 to 4, $[-CH_2]_m[NH(CH_2)_2]_nNH-CH_2]_m$ (e)

wherein m is 1 or 2 and n is a positive integer from 1 to 4, $+CH_2+_m-NH(CH_2)_4NH(CH_2)_3NH+CH_2+_m$ (f)

where m is 1 or 2, $+CH_2+_mNH(CH_2)_3NH(CH_2)_4NH(CH_2)_3NH+CH_2+_m$ (g)

where m is 1 or 2, $+CH_2+_m[NH(CH_2)_p]_nNH+CH_2+_m$ (h)

where m is 1 or 2 and n and p are positive integers from 1 to 4 which may be alike or different, $+CH_2+_m[NH(CH_2)_x]_a[NH(CH_2)_y]_b[NH(CH_2)_z]_cNH+CH_2+_m$ (i)

where m is 1 or 2 and a,b,c,x,y, and z are positive integers from 1 to 4 which may be alike or different or

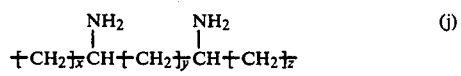 (j)

wherein x,y, and z represent positive integers from 1 to 5 which may be alike or different and pharmacologically acceptable salts thereof.

Especially preferred compounds of the present invention are represented by the formula

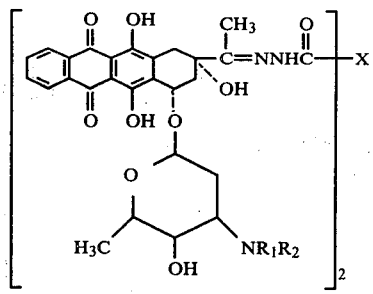

wherein $R_1$ and $R_2$ are defined as herein before and X represents

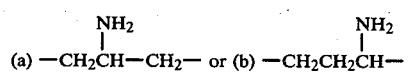

and the pharmacologically acceptable salts thereof.

DETAILED DESCRIPTION OF THE INVENTION

The compounds of the present invention are conveniently prepared as illustrated in Scheme I wherein $R_1$, $R_2$ and X are as previously defined.

Scheme I

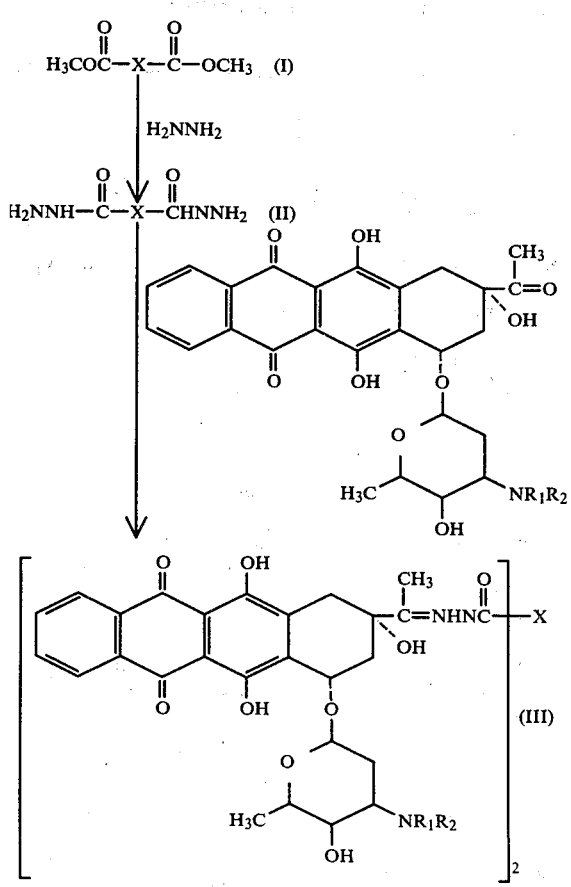

Thus the diester (I) is contacted with hydrazine or its hydrate to give the dihydrazide (II) which is coupled with the 4-demethoxydaunorubicin derivative to give the final product, a bis(4-demethoxydaunorubicin)dihydrazone (III). The synthesis of 4-demethoxydaunorubicin is described in U.S. Pat. No. 4,046,878 and F. Arcamone, et al. CANCER TREATMENT REPORTS, 60 (7): 829–834 (1976).

When the bis(4-demethoxydunorubicin)dihydrazone is obtained in the form of a salt the free base may be prepared by dissolving the salt in water and adding an equivalent amount of alkali. This will cause the precipitation of the free base which may then be recovered by standard procedures.

The diesters may be prepared by conventional esterifiying techniques. The bridging group represented by X may be alkylene having from 3 to 20 carbon atoms and optionally substituted by one or more hydroxy and/or primary amino groups. Methods for the preparation of various hydroxy and/or amino substituted alkanes may be found in preparative organic chemistry textbooks such as Wagner and Zook, SYNTHETIC ORGANIC CHEMISTRY (1953), John Wiley & Sons, Inc., New York.

The bridging group X, may also be alkylene optionally interrupted by one or more secondary amino groups, the total number of carbon and nitrogen atoms in the resultant chain being from 3 to 20. The diesters for these compounds may be prepared according to the procedure outlined in Scheme II. The following compounds which may be used as the starting material in Scheme II are commercially available:

$NH_2(CH_2)_2NH_2$
$NH_2(CH_2)_2NH(CH_2)_2NH_2$
$NH_2(CH_2)_2NH(CH_2)_2NH(CH_2)_2NH_2$
$NH_2(CH_2)_2NH(CH_2)_2NH(CH_2)_2NH(CH_2)_2NH_2$
$NH_2(CH_2)_4NH(CH_2)_3NH_2$ (Spermidine)
$NH_2(CH_2)_3NH(CH_2)_4NH(CH_2)_3NH_2$ (Spermine)

Scheme II

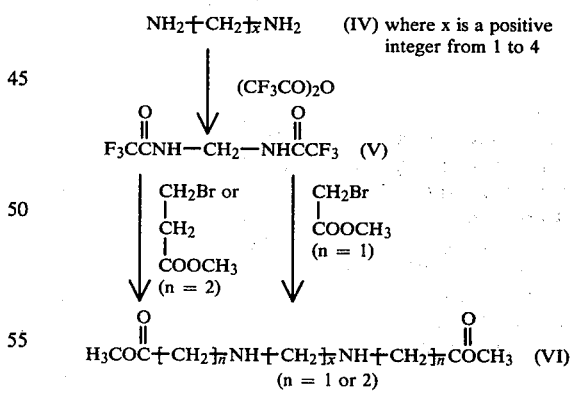

Thus the alkylene diamine (IV) is contacted with trifluoroacetic anhydride to give the N-substituted trifluoroacetyl compound (V) which is contacted with methyl bromoacetate or methyl 3-bromopropionate in the presence of potassium hydride to form the diester (VI) after selective hydrolysis of the trifluoroacetyl groups.

Compounds of the present invention are useful by reason of their valuable biological properties. They are potent antineoplastic agents.

Antineoplastic activity of compounds of the present invention is illustrated by the P-388 leukemia test described in M. A. Apple, et. al., CANCER CHEMOTHERAPY REPORTS 51 (7): 455–464 (1967) and M. A. Apple, et. al., U.S. Pat. No. 4,118,482. The P-388 leukemia test is designed to reveal promising antineoplastic drugs. J. F. Holland and E. Frei, CANCER MEDICINE, Lea & Febiger, Philadelphia (1975).

The antineoplastic activity of bis(4-demethoxydaunorubicin) 3-amino-1,5-dioxopentane-1,5-diyl dihydrazone, [Test Compound (T)], was evaluated in the P-388 leukemia test as follows Donor mice were implanted with P-388 leukemia cells IP. On the sixth day following implant the mice were sacrificed. Tumor cells were collected from the peritoneal cavity suspended in an isotonic salt solution and $10^6$ cells per mouse were implanted into mice (18–20 gram $B_6D_2F_1$ males). A single injection of the test compound was given 24 hours following the implant of tumor cells. The animals were observed and the survival pattern was compared with that of control mice which received the same tumor implant but were not given any treatment. Results are presented as % T/C (% Test/Control). Any T/C of greater than 25% is considered significant. Results as high as 175% have correlated well with ultimate success as a drug agent in human solid cancers as well as leukemias. The T/C of 175% shown by the test compound (T) in Table 1 is comparable to adriamycin in P-388 and superior to daunorubicin, two effective drugs now in use for cancer chemotherapy. The compounds of the present invention are administered in the same manner and at similar dosage levels as adriamycin in the management of neoplastic disease.

TABLE 1

| Test Compound (T) [Example 3] | | |
|---|---|---|
| Dose | Survival | % T/C |
| No drug (Control, C) | 12 days | — |
| 22 mg/kg | 4 days | Toxic |
| 6.6 mg/kg | 15 days | 125% |
| 2.1 mg/kg | 21 days | 175% |

Antiviral activity of compounds of the present invention is illustrated by testing the compounds substantially as described in M. A. Apple, ANNUAL REPORTS OF MEDICINAL CHEMISTRY, Vol. 8, p. 251–256, Academic Press (1973). When the antiviral activity of bis (4-demethoxydaunorubicin) 3-amino-1,5-dioxopentane-1,5-diyl dihydrazone trihydrochloride (Example 3) was evaluated in the above test using daunorubicin as an index compound, it was found to be about 50 times more potent as an inhibitor of reverse transcriptase activity than daunorubicin. This indicates that these compounds have substantial antiviral activity.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et. al., "Remington's Pharmaceutical Sciences", 14 Ed., Merck Publishing Company, Eaton, Pa., 1965.

The following examples are presented to further illustrate the present invention. They should not be construed as limiting it either in spirit or in scope. In these examples quantities are indicated in parts by weight unless parts by volume is specified, and temperatures are indicated in degrees Centigrade (°C.). The relationship between parts by weight and parts by volume is the same as that existing between grams and milliliters.

EXAMPLE 1

3.5 Parts 3-aminoglutaric acid dimethyl ester prepared by the method of Josey, et.al., J. ORG. CHEM. 27: 2466–2470 (1962) is dissolved in 100 parts by volume diethyl ether and anhydrous hydrogen chloride is added until the hydrochloride crystallizes. The hydrochloride salt is recrystallized from methanol ether and 1.0 part of the hydrochloride is dissolved in 5 parts by volume hydrazine hydrate. The solution is allowed to stand at room temperature overnight and the excess hydrazine hydrate is removed by distillation. The residue is washed first with ether and then with methanol. It is then dissolved in 3 parts by volume of water and recrystallized by adding 25 parts by volume methanol to give 3-amino-1,5-dioxopentane-1,5-diyl dihydrazide hydrochloride which has the following structural formula

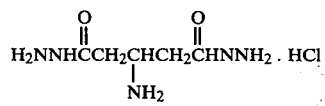

EXAMPLE 2

To 200 parts by volume of methanol which has been cooled in an ice bath is added 25 parts by volume thionyl chloride followed by 12.5 parts D-glutamic acid. The solution is refluxed for two hours then concentrated to dryness. The resulting diester is crystallized as the hydrochloride from a methanol and ether mixture.

2.0 Parts of the diester product is added to 25 parts by volume methanol which contains 10 parts by volume hydrazine hydrate and the resulting solution is refluxed overnight. The solution is concentrated to dryness and the residue is dissolved in benzene. The benzene is removed by distillation under low pressure. This is repeated three times until the product crystallizes when the benzene is removed by distillation. The product is recrystallized from methanol to give 2-amino-1,5-dioxopentane-1,5-diyl dihydrazide which has the following structural formula

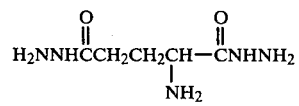

EXAMPLE 3

To 10.0 part by volume methanol is added 0.0155 parts 3-amino-1,5-dioxopentane-1,5-diyl dihydrazide hydrochloride, 0.080 part 4-demethoxydaunorubicin hydrochloride and 0.01 part by volume acetic acid. The reaction mixture is stirred for three days at room temperature then diluted with 190 parts by volume of diethyl ether. The crystalline product is collected by centrifugation and is resuspended in 30 parts by volume of 5% methanol in ether. The crystalline product is collected by centrifugation to give bis(4-demethoxydaunorubicin) 3-amino-1,5-dioxopentane-1,5-diyl dihydrazone trihydrochloride which has the following structural formula

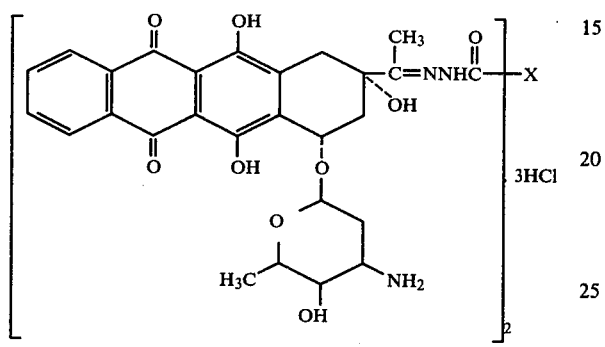

wherein X represents

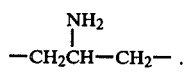

EXAMPLE 4

To 10.0 parts by volume methanol is added 0.026 part 2-amino-1,5-dioxopentane-1,5-diyl dihydrazide, 0.16 part 4-demethoxydaunorubicin hydrochloride, and 0.01 part by volume acetic acid. The reaction mixture is stirred for seven days at room temperature. The solution is concentrated under a stream of nitrogen to approximately 3 parts by volume and to it is added 1.0 part by volume of 0.57 N methanolic hydrogen chloride followed by a large volume of ether. The crystallized product is removed by filtration then crystallized from methanolether to give bis(4-demethoxydaunorubicin) 2-amino-1,5-dioxopentane-1,5-diyl dihydrazone trihydrochloride which has the following structural formula

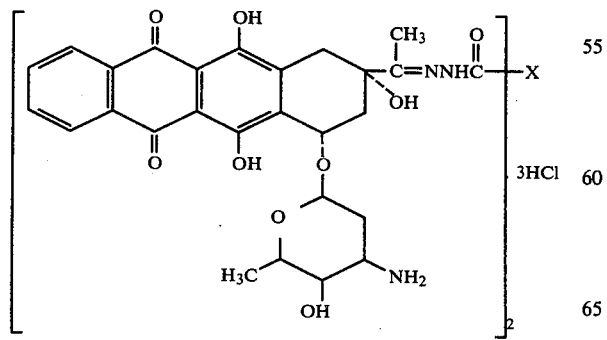

wherein X represents

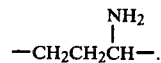

EXAMPLE 5

21.7 Parts of 3-aminoglutaric acid dimethyl ester is acetylated with 100 parts by volume acetic anhydride in 130 parts by volume pyridine to give N-acetyl-3-aminoglutaric acid dimethyl ester which has the following structural formula

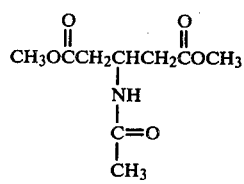

EXAMPLE 6

21.7 Parts of N-acetyl-3-aminoglutaric acid dimethyl ester in 250 parts by volume of benzene is contacted with 4.8 parts by weight sodium hydride and the reaction mixture is refluxed until no more hydrogen is evolved. The reaction mixture is carefully accidified with dilute aqueous acetic acid with cooling then washed with water. The solvent is evaporated and the product refluxed with 250 parts by volume of 10% aqueous hydrochloric acid until no more carbon dioxide evolves. The solvent is removed by evaporation under reduced pressure and the residue is esterified by stirring overnight in 250 parts by volume of methanol which contains 4 parts of hydrogen chloride and 40 parts of acetone dimethyl ketal. Removal of the solvent under reduced pressure gives the product 3,7-diamino-5-oxo-1,9-nonanedioic acid dimethyl ester dihydrochloride having the following structural formula

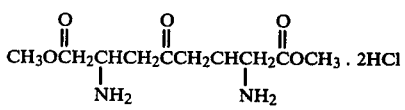

EXAMPLE 7

A solution of 1.0 part of 3,7-diamino-5-oxo-1,9-nonanedioic acid dimethyl ester dihydrochloride in 50 parts by volume of 95% ethanol containing 0.10 part platinum oxide is hydrogenated at room temperature until 1.0 mole of hydrogen is taken up. The catalyst is removed by filtration and the filtrate is concentrated to a small volume then diluted with ether. The product 3,7-diamino-5-hydroxy-1,9-nonanedioic acid dimethyl ester dihydrochloride precipitates as white crystals having the following structural formula

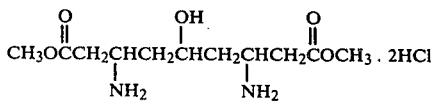

EXAMPLE 8

26 Parts 3,7-diamino-5-oxo-1,9-nonanedioic acid dimethyl ester dihydrochloride, 50 parts ammonium acetate and 4.5 parts sodium cyanoborohydride are added to 300 parts by volume methanol, and the mixture is stirred for 48 hours at room temperature. The pH is adjusted to 2.0 with concentrated hydrochloric acid, and the methanol is removed under vacuum. The residue is dissolved in 100 ml. of water, and the pH is adjusted to 10 to 12 with solid potassium hydroxide after which the solution is saturated with sodium chloride and extracted repeatedly with ethyl acetate. The combined extracts are dried with sodium sulfate and concentrated to dryness under reduced pressure. The hydrochloride is prepared by dissolving the residue in methanol and bubbling hydrogen chloride through the solution until the pH reaches 2.0. Ethyl ether is added to precipitate the hydrochloride salt. The product is recrystallized from ethanol-ether to provide 3,5,7-triamino-1,9-nonanedioic acid dimethyl ester trihydrochloride which has the following structural formula

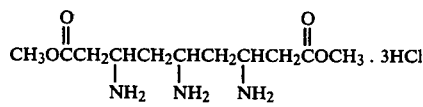

EXAMPLE 9

2.0 parts by weight 3,7-diamino-5-hydroxy-1,9-nonanedioic acid dimethyl ester dihydrochloride and 10 parts by volume hydrazine hydrate are added to 25 parts by volume methanol. The mixture is refluxed overnight. The methanol and excess hydrazine hydrate are removed by evaporation under reduced pressure and the product is recrystallized from methanol to give 3,7-diamino-5-hydroxy-1,9-dixononane-1,9-diyl dihydrazide dihydrochloride which has the following structural formula

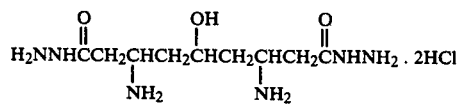

EXAMPLE 10

Substitution of an equivalent quantity of 3,7-diamino-5-hydroxy-1,9-dioxononane-1,9-diyl dihydrazide dihydrochloride for the 3-amino-1,5-dioxopentane-1,5-diyl dihydrazide hydrochloride called for in Example 3 and substantial repetition of the procedures detaild therein provides bis(4-demethoxydaunorubicin)-3,7-diamino-5-hydroxy-1,9-dioxononane-1,9-diyl dihydrazone tetrahydrochloride which has the following structural formula

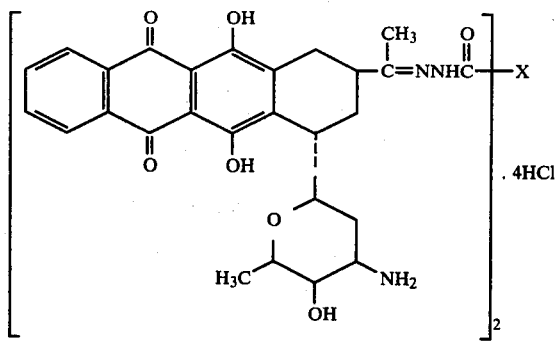

wherein X represents

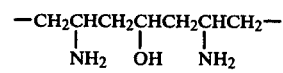

EXAMPLE 11

Substitution of an equivalent quantity of 3,5,7-triamino-1,9-nonanedioic acid dimethyl ester trihydrochloride for the 3,7-diamino-5-hydroxy-1,9-nonanedioic acid dimethyl ester dihydrochloride of Example 9 and substantial repetition of the procedures detailed therein provides 3,5,7-triamino-1-9-dioxononane-1,9-diyl dihydrazide trihydrochloride which has the following structural formula

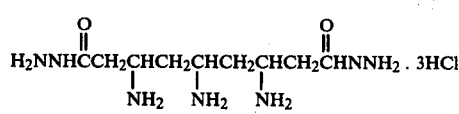

EXAMPLE 12

Substitution of an equivalent quantity of 3,5,7-traimino-1,9-dioxononane-1,9-diyl dihydrazide trihydrochloride for the 3-amino-1,5-dioxopentane-1,5-diyl dihydrazide hydrochloride called for in Example 3 and substantial repetition of the procedures detailed therein provides bis(4-demethoxydaunorubicin) 3,5,7-triamino-1,9-dioxononane-1,9-diyl dihydrazone pentahydrochloride which has the following structural formula

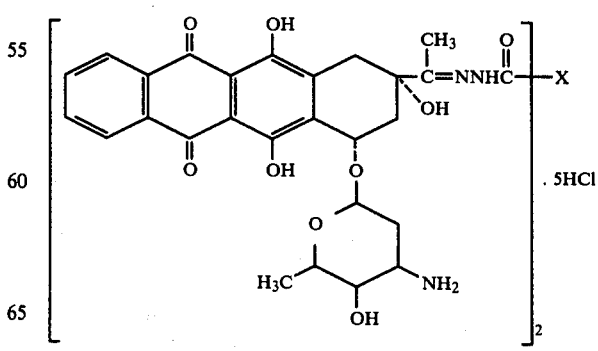

wherein X represents

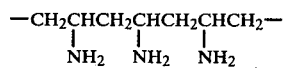

EXAMPLE 13

Substitution of an equivalent quantity of 3,7-diamino-5-hydroxy-1,9-nonanedioic acid dimethyl ester dihydrochloride for the 3-aminoglutaric acid dimethyl ester called for in Example 5 and substantial repetition of the procedures detailed therein provides 3,7-diacetylamino-5-hydroxy-1,9-nonanedioic acid dimethyl ester which has the following structural formula

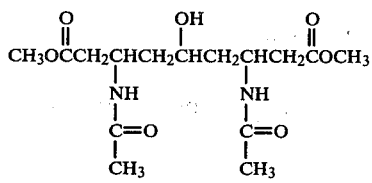

When an equivalent quantity of 3,7-diacetylamino-5-hydroxy-1,9-nonanedioic acid dimethyl ester is substituted for the N-acetyl-3-aminoglutaric acid dimethyl ester of Example 6 and the procedures detailed therein substantially repeated there is obtained 3,7,11,15-tetramino-5,13-dihydroxy-9-oxo-1,17 heptadecanedioic acid dimethyl ester tetrahydrochloride which has the following structural formula

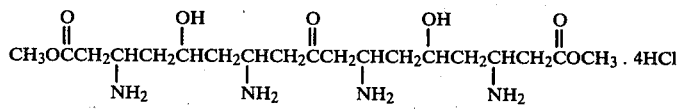

EXAMPLE 14

Substitution of an equivalent quantity of 3,7,11,15-tetraamino-5,13-dihydroxy-9-oxo-1,17 heptadecanedioic acid dimethyl ester tetrahydrochloride for the 3,7-diamino-5-oxo-1,9-nonanedioic acid dimethyl ester dihydrochloride of Example 7 and substantial repetition of the procedures described therein gives 3,7,11,15-tetraamino-5,9,13-trihydroxy-1,17-heptadecanedioic acid dimethyl ester tetrahydrochloride which has the following structural formula

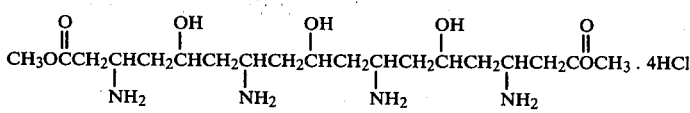

EXAMPLE 15

1.0 Part 3,7,11,15-tetraamino-5,9,13-dihydroxy-1,17-heptadecanedioic acid dimethyl ester tetrahydrochloride is dissolved in a mixture of 20 parts by volume methanol and 10 parts by volume hydrazine hydrate and the solution is refluxed overnight. The solution is concentrated to dryness and the residue is crystallized from methanol to give 3,7,11,15-tetraamino-5,9,13-trihydroxy-1,17-dioxoheptadecane-1,17-diyl dihydrazide tetradrochloride which has the following structural formula

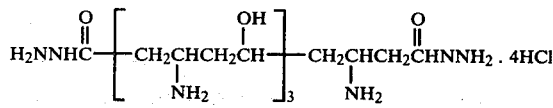

EXAMPLE 16

Substitution of an equivalent quantity of 3,7,11,15-tetraamino-5,9,13-trihydroxy-1,17-dioxoheptadecane-1,17-diyl dihydrazide of Example 3 and substantial repetition of the procedures detailed therein gives bis(4-demethoxydaunorubicin) 3,7,11,15-tetraamino-5,9,13-trihydroxy-1,17-dioxoheptadecane-1,17-diyl dihydrazone hexahydrochloride which has the following structural formula

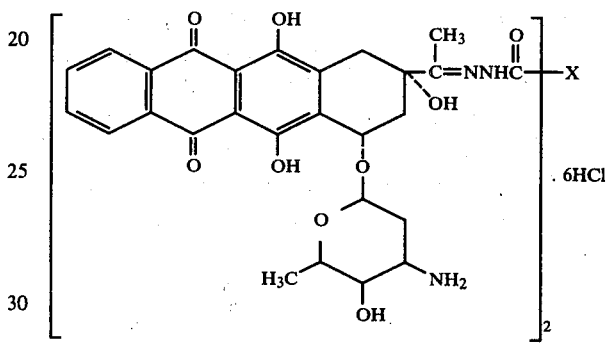

wherein X represents

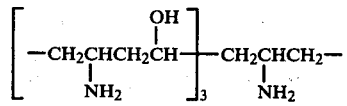

EXAMPLE 17

Substitution of an equivalent quantity of 3,5,7-triamino-1,9-nonanedioic acid dimethyl ester for the 3-aminoglutaric acid dimethyl ester called for in Example 5 and substantial repetition of the procedures detailed in Examples 5, 6, and 8 provides 3,5,7,9,11,13,15-heptamino-1,17-heptadecanedoic acid dimethyl ester heptahydrochloride which has the following structural formula

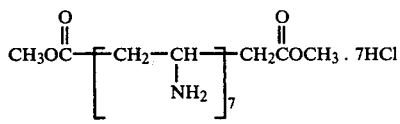

EXAMPLE 18

1.0 Part 3,5,7,9,11,13,15-heptaamino-1,17-heptadecanedioic acid dimethyl ester heptahydrochloride is dissolved in a mixture of 20 parts by volume of methanol and 10 parts by volume hydrazine hydrate and the solution is refluxed overnight then concentrated to dryness under reduced pressure to give 3,5,7,9,11,13,15-heptaamino-1,17-dioxoheptadecane-1,17-diyl dihydrazide heptahydrochloride which has the following structural formula

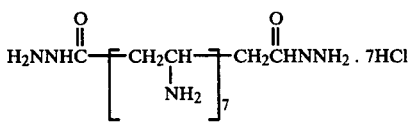

EXAMPLE 19

Substitution of an equivalent quantity of 3,5,7,9,11,13,15-heptaamino-1,17-dioxoheptadecane-1,17-diyl dihydrazide heptahydrochloride for the 3-amino-1,5-dioxopentane-1,5-diyl dihydrazide hydrochloride called for in Example 3 and substantial repetition of the procedures detailed therein provides bis(4-dimethoxydaunorubicin) 3,5,7,9,11,13,15-heptaamino-1,17-dioxoheptadecane-1,17-diyl dihydrazone nonahydrochloride which has the following structural formula

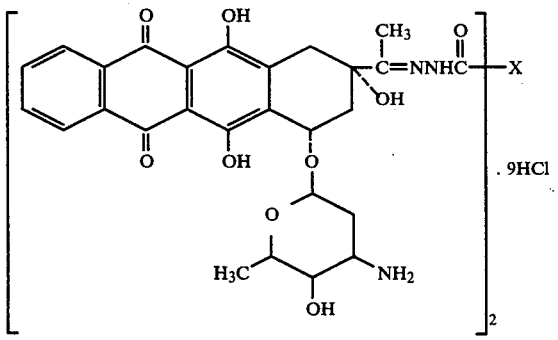

wherein X represents

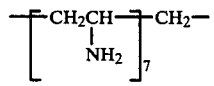

EXAMPLE 20

1.0 Part of 6,12-dioxo-1,17-heptadecanedoic acid prepared according to the method described in German Pat. No. 1,070,163, Dec. 3, 1959 (CHEM. ABS. 55, NO. 10326) is esterified by dissolving it in a mixture of 100 parts by volume methanol and 10 parts by volume thionyl chloride. The solution is refluxed for 4 hours and concentrated to a small volume resulting in the precipitation of the dimethyl ester, 6,12-dioxo-1,17 heptadecanedioic acid dimethyl ester which has the the following structural formula

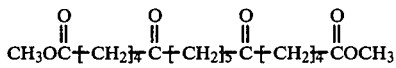

When an equivalent quantity of 6,12-dioxo-1,17 heptadecanedioic acid dimethyl ester is substituted for the 3,7-diamino-5-oxo-1,9-nonanedioic acid dimethyl ester dihydrochloride called for in Example 8 and the procedures therein substantially repeated there is obtained 6,12-diamino-1,17-heptadecanedioic acid dimethyl ester which has the following structural formula

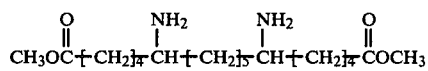

Substitution of an equivalent quantity of 6,12-diamino-1,17-heptadecanedioic acid dimethyl ester for the 3,7-diamino-5-hydroxy-1,9-nonanedioic acid dimethyl ester called for in Example 9 and substantial repetition of the procedures detailed therein provides 6,12-diamino-1,17-dioxoheptadecane-1,17-diyl dihydrazide which has the following structural formula

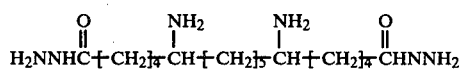

Substitution of an equivalent quantity of 6,12-diamino-1,17-dioxoheptadecane-1,17-diyl dihydrazide for the 3-amino-1,5-dioxopentane-1,5-diyl dihydrazide hydrochloride and substantial repetition of the procedures described in Example 3 provides bis(4-dimethoxydaunorubicin) 6,12-diamino-1,17-dioxoheptadecane-1,17-diyl dihydrazone tetrahydrochloride which has the following structural formula

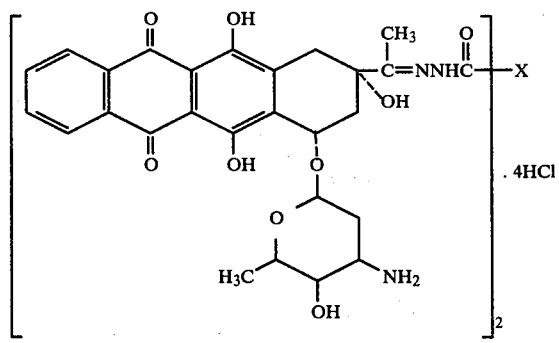

wherein X represents

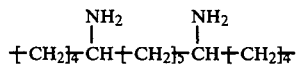

EXAMPLE 21

1.0 Part of N,N'-bis(3-aminopropyl)-1,4-butanediamine is dissolved in 50 parts by volume of diethyl ether. To this solution is added 8 parts by volume of trifluoroacetic anhydride. The solution is allowed to stand overnight at room temperature then washed with water followed by washes with aqueous potassium bicarbonate and another wash with water. Evaporation of the solvent yields N,N'-trifluoroacetyl-N,N'-bis(3-trifluoroacetylaminopropyl)-1,4-butanediamine which has the following structural formula

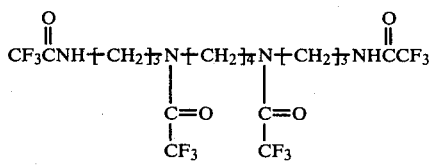

EXAMPLE 22

To a mixture of 50 parts by volume benzene and 10 parts by volume dry tetrahydrofuran is added 0.028 part potassium hydride followed by the gradual addition of 2.9 parts N,N'-trifluoroacetyl-N,N'-bis(3-trifluoroacetylaminopropyl)-1,4-butanediamine. When the evolution of hydrogen ceases 0.05 part of 18-crown-6 and 1.7 parts methyl bromoacetate is added. The reaction mixture is stirred for 4 hours at room temperature then refluxed overnight. The solvent is removed by distillation under low pressure followed by drying of the residue under high vacuum. To the residue is added 50 parts by volume hydrazine hydrate. The reaction mixture is stirred overnight at room temperature. Removal of the solvent under reduced pressure followed by crystallization from aqueous ethanol gives 1,18-dioxo-3,7,12,16-tetrazaoctadecane-1,18-diyl dihydrazide which has the following structural formula

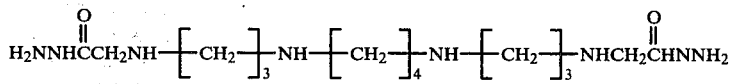

EXAMPLE 23

Substitution of an equivalent quantity of 1,18-dioxo-3,7,12,16-tetraazaoctadecane-1,18-diyl dihydrazide for the 3-amino-1,5-dioxopentane-1,5-diyl dihydrazide called for in Example 3 and substantial repetition of the procedures detailed therein provides bis(4-demethoxydaunorubicin) 1,18-dioxo-3,7,12,16-tetraazaoctadecane-1,18-diyl dihydrazone hexahydrochloride which has the following structural formula

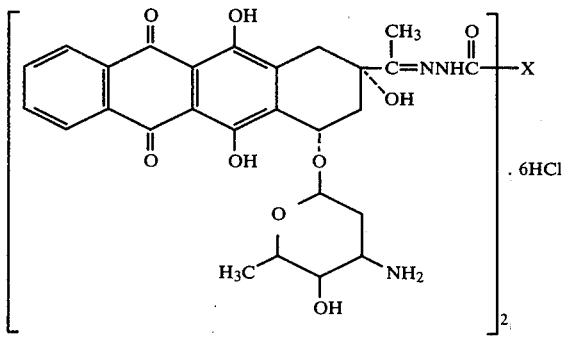

wherein X represents

EXAMPLE 24

Methyl N-acetyl-β-daunosamine is prepared according to the method described in D. Horton and W. Weckerle, CARBOHYDRATE RESEARCH:44:2-27-240(1975) 2.0 Parts of methyl-N-acetyl-β-daunosamine is dissolved in 40 parts by volume of water and 6.3 parts barium hydroxide hydrate is added with stirring. The solution is refluxed for 24 hours. After cooling the solution solid carbon dioxide pellets are added. The barium carbonate which forms is removed by filtration and the solution is reduced to dryness under high vacuum at 25° C. The resulting solid is partially dissolved in 2β-ethanol and filtered. The ethanol is removed under vacuum to give methyl-β-daunosamine acetate which has the following structural formula

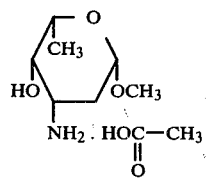

EXAMPLE 25

A mixture of 0.34 part by volume formic acid and 0.82 part by volume acetic anhydride are heated under nitrogen at 50° C. for 2 hours then cooled to room temperature. The resulting solution is added to a solution of 1.77 parts of the methyl-β-daunosamine acetate from Example 24 dissolved in 20 parts by volume pyridine. The resulting solution is stirred at room temperature for 30 minutes then poured into 40 parts by volume of water. The aqueous solution is neutralized with 1 N sodium hydroxide and reduced to dryness under high vacuum at 25° C. The residue is extracted with dichloromethane, washed with saturated sodium chloride solution, dried over magnesium sulfate, filtered and reduced to dryness to give methyl-N-formyl-β-daunosamine which has the following structural formula

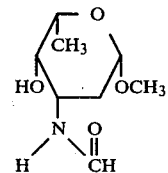

EXAMPLE 26

0.38 Part of methyl N-formyl-β-daunosamine is dissolved in 10 parts by volume anhydrous tetrahydrofuran under argon. To this solution is added 6.3 parts by volume of a solution of 0.95 M lithium aluminum hydride in tetrahydrofuran and the resulting clear solution is stirred overnight. The reaction is quenched by adding 0.23 parts by volume water followed by 0.23 parts by volume 15% sodium hydroxide solution and 0.69 parts by volume water. The solution is filtered and reduced to dryness under vacuum. The product is partially dissolved in ether and a small amount of starting material removed by filtration. The solvent is removed under vacuum to yield methyl N-methyl-β-daunosamine which has the following structural formula

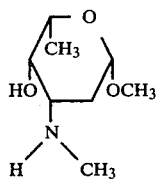

EXAMPLE 27

1.0 Part of methyl N-methyl-β-daunosamine is dissolved in 60 parts by volume of anhydrous ether under argon, with stirring, and cooled to 5°–10° C. 8.0 ml of trifluoroacetic anhydride is added dropwise while maintaining a temperature of 5°–10° C. After the addition is complete the solution is allowed to warm to room temperature and stand overnight. The solution is reduced to dryness under aspirator vacuum then placed under high vacuum until constant weight is achieved. The residue is dissolved in a mixture of 20% ethyl acetate/80% toluene and filtered through 20 parts by volume silicic acid (Mallinkrodt CC-7) on a sintered glass funnel to remove the dark coloring. The filtrate is reduced to dryness under vacuum to give methyl N-methyl-N-trifluoroacetyl-4-O-trifluoroacetyl-β-daunosamine which has the following structural formula

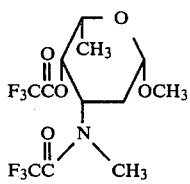

EXAMPLE 28

1.75 Parts of methyl N-methyl-N-trifluoroacetyl-4-O-trifluoroacetyl-β-daunosamine is dissolved in 25 parts by volume of methanol under argon and 10 drops of pyridine is added with stirring. The solution is stirred for two hours at room temperature and reduced to dryness under vacuum. The crude product is filtered through a small column of silicic acid using a 50% ethyl acetate/50% toluene medium as eluant. The eluate to collected and reduced to dryness under vacuum to give methyl N-methyl-N-trifluoroacetyl-β-daunosamine which has the following structural formula

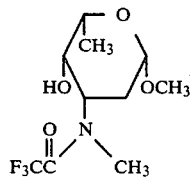

EXAMPLE 29

0.271 Part of methyl N-methyl-N-trfluoroacetyl-β-daunosamine is dissolved in 3.0 parts by volume anhydrous dichloromethane under argon. 0.3 Part by volume trifluoroacetic acid is added and the solution is stirred under argon overnight. The solution is blown to dryness under argon then dried to constant weight under vacuum. The crude residue is extracted with ether three times and the ether extractions are collected and blown to dryness under argon. The residue is dried to constant weight under vacuum to give N-methyl-N-trifluoroacetyl-β-daunosamine which has the following structural formula

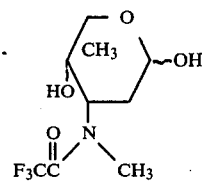

EXAMPLE 30

0.129 Part of N-methyl-N-trifluoroacetyl-β-daunosamine is dissolved in 3.5 part by volume pyridine under argon at room temperature. To this solution is added 0.290 part of p-nitrobenzoylchloride and the resulting solution is stirred for 3 hours. The solution is cooled to 5° C. and 3.5 parts by volume of water is added dropwise while maintaining a temperature of 5°–10° C. The resulting product is collected by filtration, washed with water and dried under vacuum to give N-methyl-N-trifluoroacetyl-1,4-bis(O-p-nitrobenzoate)-β-daunosamine which has the following structural formula

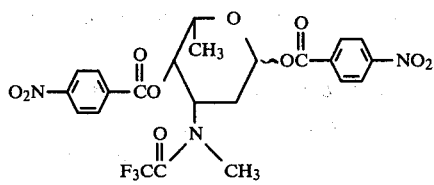

Following the procedure described in E. M. Acton, et.al., J.MED.CHEM. 17 (6): 659–660(1974), N-methyl-N-trifluoroacetyl-1,4-bis(O-p-nitrobenzoate)-β-daunosamine is converted to N-methyl-N-trifluoroacetyl-1-bromo-4-O-p-nitrobenzoate-β-daunosamine which is then coupled with 4-demethoxydaunomycinone to give N-methyl-4-demethoxydaunorubicin hydrochloride which has the following structural formula

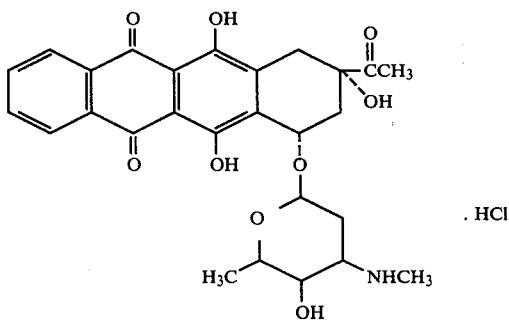

EXAMPLE 31

Substitution of N-methyl-4-demethoxydaunorubicin hydrochloride for the 4-demethoxydaunorubicin hydrochloride of Example 3 and substantial repetition of the procedures detailed therein gives bis(N-methyl-4-demethoxydaunorubicin) 3-amino-1,5-dioxopentane-1,5-diyl dihydrazone trihydrochloride which has the following structural formula

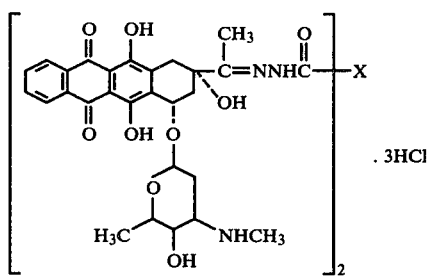

wherein X represents

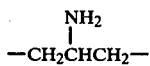

EXAMPLE 32

Substitution of N-methyl-4-demethoxydaunorubicin hydrochloride for the 4-demethoxydaunorubicin hydrochloride of Example 4 and substantial repetition of the procedures detailed therein gives bis(N-methyl-4-demethoxydaunorubicin) 2-amino-1,5-dioxopentane-1,5-diyl dihydrazone trihydrochloride which has the following structural formula

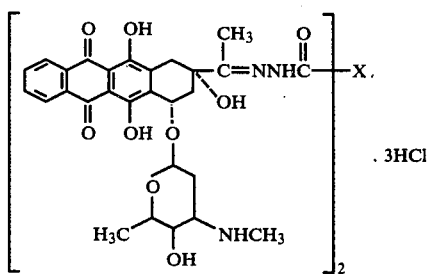

wherein X represents

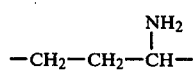

What is claimed is:

1. A compound of the formula

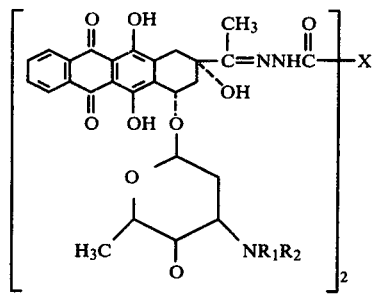

and pharmacologically acceptable salts thereof wherein $R_1$ and $R_2$ represent hydrogen or alkyl having from 1 to 4 carbon atoms and X represents
   (a) Alkylene having from 3 to 20 carbon atoms and optionally substituted by one or more hydroxy or primary amino groups or both, or
   (b) Alkylene optionally interrupted by one or more secondary amino groups, the total number of carbon and nitrogen atoms in the resultant chain being from 3 to 20.

2. A compound according to claim 1 of the formula

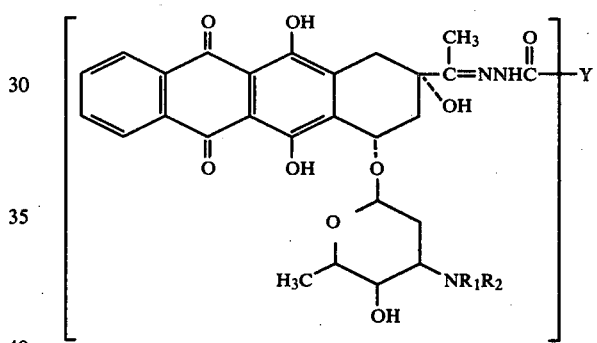

and pharmacologically acceptable salts thereof wherein $R_1$ and $R_2$ represent hydrogen or alkyl having 1 to 4 carbon atoms and Y represents

 (a)

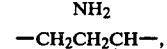 (b)

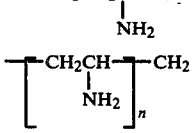 (c)

wherein n is a positive integer from 1 to 9, $$\left[\begin{array}{c}-CH_2CHCH_2CH-\\ | \quad\quad | \\ NH_2 \quad OH\end{array}\right]_n -CH_2CHCH_2- \atop NH_2 \quad\quad\quad\quad (d)$$

wherein n is a positive integer from 1 to 4

$+CH_2+[NH(CH_2)_2]_{\overline{n}}NH+CH_2+_{\overline{m}}$  (e)

wherein m is 1 or 2 and n is a positive integer from 1 to 4

$+CH_2+_{\overline{m}}NH(CH_2)_4NH(CH_2)_3NH+CH_2+_{\overline{m}}$  (f)

wherein m is 1 or 2,

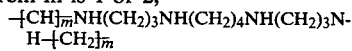 (g)

wherein m is 1 or 2

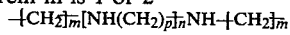 (h)

wherein m is 1 or 2 and n and p are positive integers from 1 to 4 which may be alike or different,

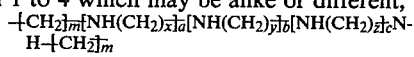 (i)

wherein m is 1 or 2 and a,b,c,x,y, and z are positive integers from 1 to 4 which may be alike or different or

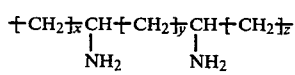 (j)

wherein x,y, and z are positive integers from 1 to 5 which may be alike or different.

3. A compound according to claim 1 which is a pharmacologically acceptable salt of bis(4-demethoxydaunorubicinic) 3-amino-1,5-dioxo-pentane-1,5-diyl dihydrazone.

4. A compound according to claim 1 which is a pharmacologically acceptable salt of bis(4-demethoxydaunorubicin) 2-amino-1,5-dioxo-pentane-1,5-diyl dihydrazone.

5. A compound according to claim 1 which is bis(4-demethoxydaunorubicin) 3-amino-1,5-dioxopentane-1,5-diyl dihydrazone trihydrochloride.

6. A compound according to claim 1 which is bis(4-demethoxydaunorubicin) 2-amino-1,5-dioxopentane-1,5-diyl dihydrazone trihydrochloride.

7. A compound according to claim 1 which is bis(4-demethoxydaunorubicin) 3-amino-1,5-dioxopentane-1,5-diyl dihydrazone.

8. A compound according to claim 1 which is bis(4-demethoxydaunorubicin) 2-amino-1,5-dioxopentane-1,5-diyl dihydrazone.

* * * * *